US00PP22372P2

(12) United States Plant Patent
Goemans

(10) Patent No.: US PP22,372 P2
(45) Date of Patent: Dec. 20, 2011

(54) ***ALSTROEMERIA* PLANT NAMED 'LUCY'**

(50) Latin Name: *Alstroemeria hybrida*
Varietal Denomination: Lucy

(75) Inventor: Francis Cornelius Goemans, Chichester (GB)

(73) Assignee: Wülfinghoff Alstroemeria B.V., Rijswijk (NL)

( * ) Notice: Subject to any disclaimer, the term of this patent is extended or adjusted under 35 U.S.C. 154(b) by 0 days.

(21) Appl. No.: 12/806,248

(22) Filed: Aug. 7, 2010

(51) Int. Cl.
*A01H 5/00* (2006.01)

(52) U.S. Cl. ..... Plt./309

(58) Field of Classification Search ..... Plt./309
See application file for complete search history.

*Primary Examiner* — Susan McCormick Ewoldt
(74) *Attorney, Agent, or Firm* — C. A. Whealy

(57) ABSTRACT

A new and distinct cultivar of *Alstroemeria* plant named 'Lucy', characterized by its compact and mounding plant habit; sturdy and strong plants; vigorous growth habit; large pink and yellow-colored flowers; and good garden performance.

2 Drawing Sheets

Botanical designation: *Alstroemeria hybrida.*
Cultivar denomination: 'LUCY'.

BACKGROUND OF THE INVENTION

The present invention relates to a new and distinct cultivar of *Alstroemeria* plant, botanically known as *Alstroemeria hybrida,* grown typically as a potted garden *Alstroemeria,* and hereinafter referred to by the name 'Lucy'.

The new *Alstroemeria* plant is a product of a planned breeding program conducted by the Inventor in Chichester, England. The objective of the breeding program is to create new compact potted garden *Alstroemeria* cultivars that have attractive foliage and flower coloration.

The new *Alstroemeria* plant originated from a cross-pollination made by the Inventor in Chichester, England in June, 2004, of a proprietary selection of *Alstroemeria hybrida* identified as code number T38, not patented, as the female, or seed, parent with a proprietary *Alstroemeria hybrida* selection identified as code number 1205/35, not patented, as the male, or pollen, parent. The new *Alstroemeria* plant was discovered and selected by the Inventor as a flowering plant from within the progeny of the stated cross-pollination in a controlled greenhouse environment in Chichester, England in May, 2006.

Asexual reproduction of the new *Alstroemeria* plant by tissue culture in a controlled greenhouse environment in Chichester, England since October, 2008, has shown that the unique features of this new *Alstroemeria* plant are stable and reproduced true to type in successive generations.

SUMMARY OF THE INVENTION

Plants of the new *Alstroemeria* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Lucy'. These characteristics in combination distinguish 'Lucy' as a new and distinct cultivar of *Alstroemeria* plant:

1. Compact and mounding plant habit.
2. Sturdy and strong plants.
3. Vigorous growth habit.
4. Large pink and yellow-colored flowers.
5. Good garden performance.

Plants of the new *Alstroemeria* can be compared to plants of the female parent selection. Plants of the new *Alstroemeria* differ from plants of the female parent selection in the following characteristics:

1. Plants of the new *Alstroemeria* are more compact than plants of female parent selection.
2. Plants of the new *Alstroemeria* and female parent selection differ in flower color as plants of female parent selection have pale pink-colored flowers.

Plants of the new *Alstroemeria* can be compared to plants of the male parent selection. Plants of the new *Alstroemeria* differ from plants of the male parent selection in the following characteristics:

1. Plants of the new *Alstroemeria* are more compact than plants of the male parent selection.
2. Plants of the new *Alstroemeria* and the male parent selection differ in flower color as plants of the male parent selection have pale yellow-colored flowers.

Plants of the new *Alstroemeria* can be compared to plants of the *Alstroemeria hybrida* 'Natalie', disclosed in U.S. Plant Pat. No. 17,801. In side-by-side comparisons conducted in Chichester, England, plants of the new *Alstroemeria* differed from plants of 'Natalie' in the following characteristics:

1. Plants of the new *Alstroemeria* were shorter than plants of 'Natalie'.
2. Plants of the new *Alstroemeria* had smaller flowers than plants of 'Natalie'.
3. Plants of the new *Alstroemeria* and 'Natalie' differed in flower color as plants of 'Natalie' had white and red-colored flowers.

BRIEF DESCRIPTION OF THE PHOTOGRAPHS

The accompanying colored photographs illustrate the overall appearance of the new *Alstroemeria* plant showing the colors as true as it is reasonably possible to obtain in colored reproductions of this type. Colors in the photographs may differ slightly from the color values cited in the detailed botanical description which accurately describe the colors of the new *Alstroemeria* plant.

The photograph on the first sheet comprises a side perspective view of a typical flowering plant of 'Lucy' grown in a container.

The photograph on the second sheet is a close-up view of a typical flower of 'Lucy'.

DETAILED BOTANICAL DESCRIPTION

The aforementioned photographs and following observations and measurements describe plants of the new *Alstroemeria* grown during the summer in 21-cm containers in a glass-covered greenhouse in Chichester, England and under typical *Alstroemeria* production conditions. During the production of the plants, day temperatures averaged 20° C. and night temperatures averaged 14° C. Plants were six months old when the photographs and description were taken. Color references are made to The Royal Horticultural Society Colour Chart, 2001 Edition, except where general terms of ordinary dictionary significance are used.

Botanical classification: *Alstroemeria hybrida* 'Lucy'.

Parentage:

*Female, or seed, parent.*—Proprietary selection of *Alstroemeria hybrida* identified as code number T38, not patented.

*Male or pollen parent.*—Proprietary selection of *Alstroemeria hybrida* identified as code number 1205/35, not patented.

Propagation:

*Type.*—By tissue culture.

*Root description.*—Medium in thickness; fleshy; color, close to 155D.

*Rooting habit.*—Moderately freely branching; dense.

*Rhizome description.*—Shape: Elongate; rounded. Length: About 6 cm. Diameter: About 1 cm. Texture: Smooth. Color: Close to 153A.

Plant description:

*Plant habit.*—Compact and mounded; freely branching, bushy appearance; sturdy and strong plants; vigorous growth habit.

*Plant height.*—About 13 cm.

*Plant diameter* (*area of spread*).—About 28 cm.

Stem description:

*Aspect.*—Mostly upright to outwardly spreading.

*Internode length.*—About 0.3 cm to 2.5 cm.

*Strength.*—Strong, sturdy.

*Texture.*—Smooth, glabrous.

*Color.*—Close to 145C and 146A.

Foliage description:

*Arrangement.*—Alternate; below the peduncles in a single whorl; sessile.

*Length, lower leaves.*—About 7 cm.

*Length, upper leaves.*—About 4 cm.

*Width, lower leaves.*—About 2.5 cm.

*Width, upper leaves.*—About 1.3 cm.

*Shape.*—Lanceolate.

*Apex.*—Acute.

*Base.*—Attenuate.

*Margin.*—Entire.

*Texture, upper and lower surfaces.*—Smooth, glabrous.

*Venation pattern.*—Parallel.

*Color.*—Developing leaves, upper surface: Close to 137A to 137B. Developing leaves, lower surface: Close to N138B. Fully expanded leaves, upper surface: Close to 139A to 139C; venation, close to 138B. Fully expanded leaves, lower surface: Close to 138B; venation, close to 139B.

Flower description:

*Flower type and habit.*—Single cup-shaped flowers arranged in compound umbels; flowers face mostly upright to outwardly; freely flowering habit; about five to eleven flowers per inflorescence; about 125 flowers develop per plant.

*Natural flowering season.*—Plants begin flowering about 6 to 14 weeks after planting; in the garden, flowering is continuous from the late spring until frost in The Netherlands.

*Fragrance.*—None detected.

*Flower longevity on the plant.*—About two to three weeks on the plant; about one to two weeks as a cut flower; flowers not persistent.

*Flower buds.*—Length: About 4.1 cm. Diameter: About 1.9 cm. Shape: Ovoid. Color: Close to 141B to 144C.

*Flower diameter.*—About 5.5 cm.

*Flower depth* (*height*).—About 4.1 cm.

*Perianth.*—Arrangement: Six arranged in two whorls, each whorl with two lateral and one median segments. Size, inner perianth: Length, lateral segments: About 4.4 cm. Width, lateral segments: About 1.6 cm. Length, median segment: About 4.1 cm. Width, median segment: About 1.7 cm. Size, outer perianth: Length, lateral segments: About 4.5 cm. Width, lateral segments: About 3 cm. Length, median segment: About 4.5 cm. Width, median segment: About 3 cm. Shape, inner perianth, lateral and median segments: Lanceolate. Shape, outer perianth, lateral and median segments: Obovate. Apex, inner perianth, lateral and median segments: Acute. Apex, outer perianth, lateral and median segments: Embedded point. Base, inner perianth, lateral and median segments: Attenuate. Base, outer perianth, lateral and median segments: Cuneate. Margin, inner perianth, lateral and median segments: Entire. Margin, outer perianth, lateral and median segments: Slightly crenate. Texture, inner and outer perianths, lateral and median segments: Smooth, glabrous. Color, inner perianth: When opening, lateral segments, upper surface: Close to 11A, towards the apex, close to 62A; stripes, close to 183A. When opening, median segment, upper surface: Close to 11A; towards the apex, close to 63B; stripes, close to 183A. When opening, lateral segments, lower surface: Close to 14C; towards the apex, close to 62C; stripes, close to 177A. When opening, median segment, lower surface: Close to 63A to 63D; stripes, close to 177A. Fully opened, lateral segments, upper surface: Close to 9B; towards the apex, close to 64D; stripes, close to N186C. Fully opened, median segment, upper surface: Close to 8D; towards the apex, close to 62B; stripes, close to N186C. Fully opened, lateral segments, lower surface: Close to 9C; towards the apex, close to 63A; stripes, close to 177C. Fully opened, median segment, lower surface: Close to 8D; stripes, close to 177C. Color, outer perianth: When opening, lateral and median segments, upper surface: Close to 68A. When opening, lateral and median segments, lower surface: Close to 73B. Fully opened, lateral and median segments, upper surface: Close to 68B; center, close to 67C; with development color becoming closer to 73B. Fully opened, lateral and median segments, lower surface: Close to 68B.

*Pedicels.*—Length: About 3 cm to 4 cm. Diameter: About 2 mm. Strength: Strong. Angle: About 15° to 20° from vertical. Texture: Smooth, glabrous. Color: Close to 144B.

*Reproductive organs.*—Stamens: Quantity per flower: Three to eight. Anther shape: Oval. Anther size: About 4 mm by 7 mm. Anther color: Close to 67C. Pollen amount: Abundant. Pollen color: Close to 146C. Pistils: Quantity per flower: One. Pistil length: About 3 cm. Style length: About 2.5 cm. Style color: Close to 70C. Stigma color: Close to 177B. Ovary color: Close to 143A.

*Fruits.*—Length: About 1 cm. Diameter: About 5 mm. Color: Close to 143A.

*Seeds.*—Seed development has not been observed.

Disease/pest resistance: Plants of the new *Alstroemeria* have not been observed to be resistant to pathogens and pests common to *Alstroemeria*.

Garden performance: Plants of the new *Alstroemeria* have been observed to have good garden performance and to tolerate wind, rain and temperatures ranging from about 1° C. to about 25° C.

It is claimed:

1. A new and distinct *Alstroemeria* plant named 'Lucy' as illustrated and described.

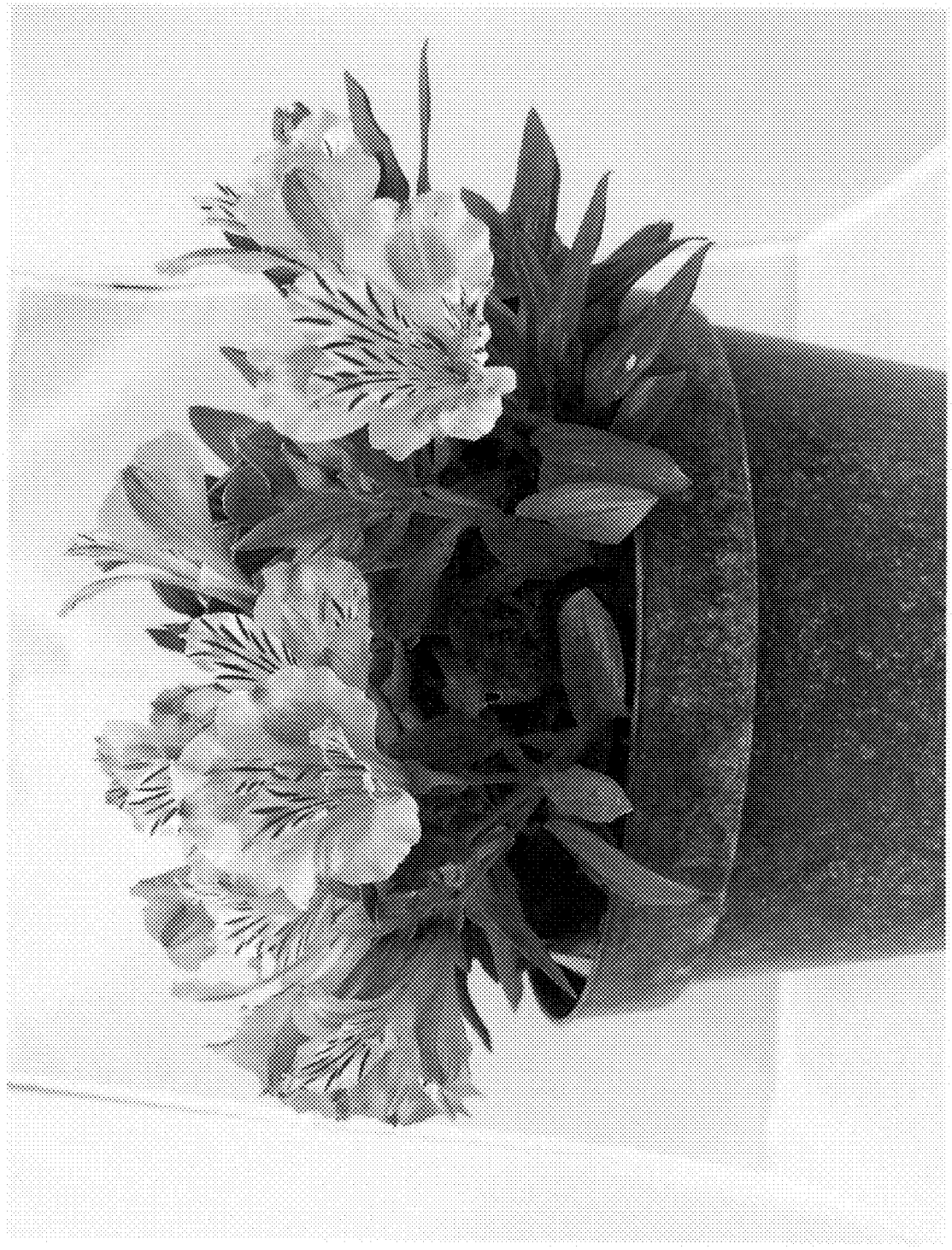

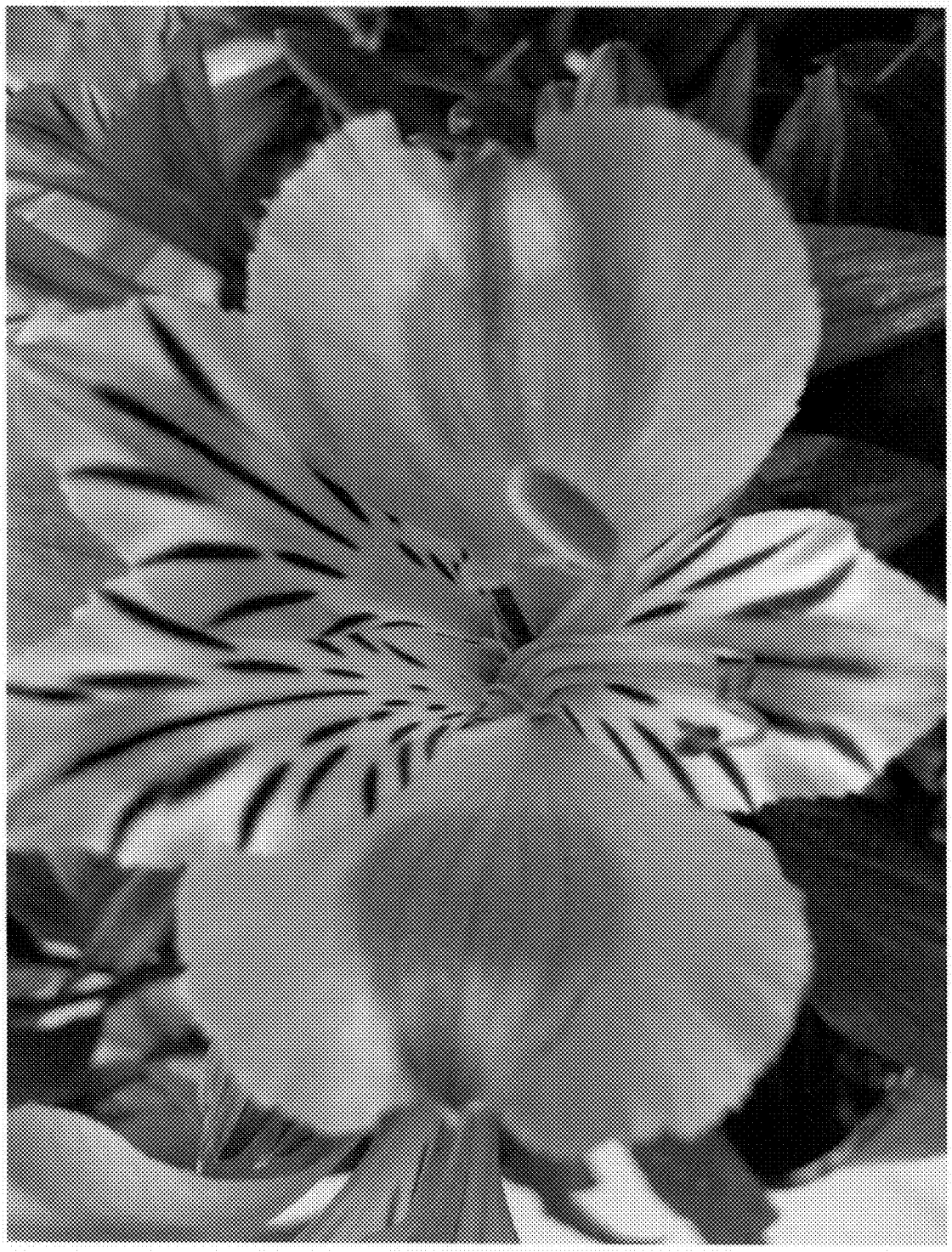

* * * * *